United States Patent [19]

Taterka et al.

[11] Patent Number: 4,779,727
[45] Date of Patent: Oct. 25, 1988

[54] CATHETER PACKAGING SYSTEM

[75] Inventors: Michael Taterka, Lake Jackson; Yue-Teh Jang, Houston; Jill J. P. Wade, Lake Jackson; Vern L. Liebmann, Sugarland, all of Tex.

[73] Assignee: Mallinckrodt, Inc., St. Louis, Mo.

[21] Appl. No.: 125,580

[22] Filed: Nov. 25, 1987

[51] Int. Cl.$^4$ ............................................. B65D 73/00
[52] U.S. Cl. .................................... 206/364; 206/370
[58] Field of Search ............... 206/364, 363, 365, 366, 206/367, 368, 369, 370

[56] References Cited

U.S. PATENT DOCUMENTS

| | | | |
|---|---|---|---|
| 3,612,038 | 10/1971 | Halligan | 206/364 |
| 3,633,758 | 1/1972 | Morse et al. | 206/364 |
| 3,926,309 | 12/1975 | Center | 206/364 |
| 3,934,721 | 1/1976 | Juster et al. | 206/364 |
| 3,978,983 | 9/1976 | Brezette | 206/364 |
| 4,248,236 | 2/1981 | Linder | 206/364 |
| 4,262,800 | 4/1981 | Nethercutt | 206/364 |
| 4,282,972 | 8/1981 | Chiulli | 206/364 |

Primary Examiner—Joseph M. Moy
Attorney, Agent, or Firm—Bernard, Rothwell & Brown

[57] ABSTRACT

A catheter packaging system includes a catheter tray having a main tray body with a hub-retaining portion and an interchangeable catheter tip-retaining insert. The insert is selectively receivable within a corresponding recess in the main tray body. The main tray body and the interchangeable insert each include a plurality of catheter tracks for holding different catheters with at least one catheter tip track of the interchangeable insert being in line with a main body track for holding a catheter therein. Each main body track is provided with a hub-retaining slot for engaging and holding a catheter hub.

16 Claims, 1 Drawing Sheet

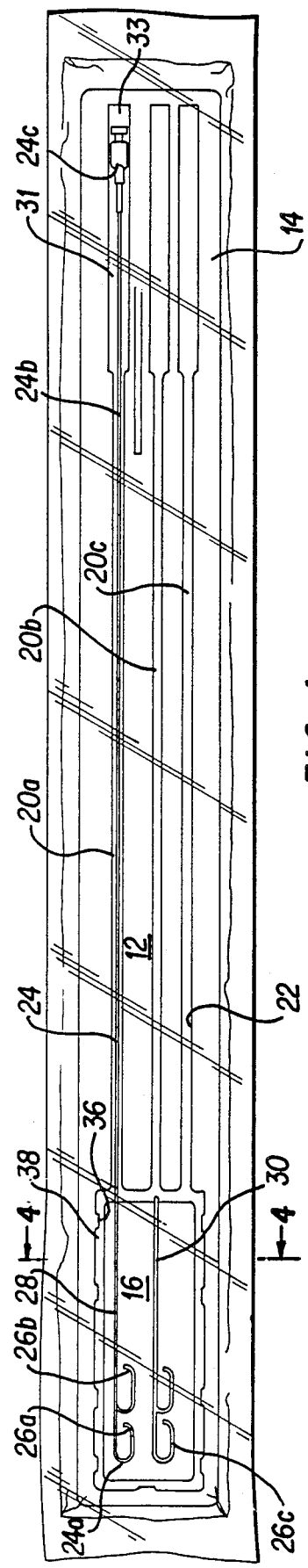
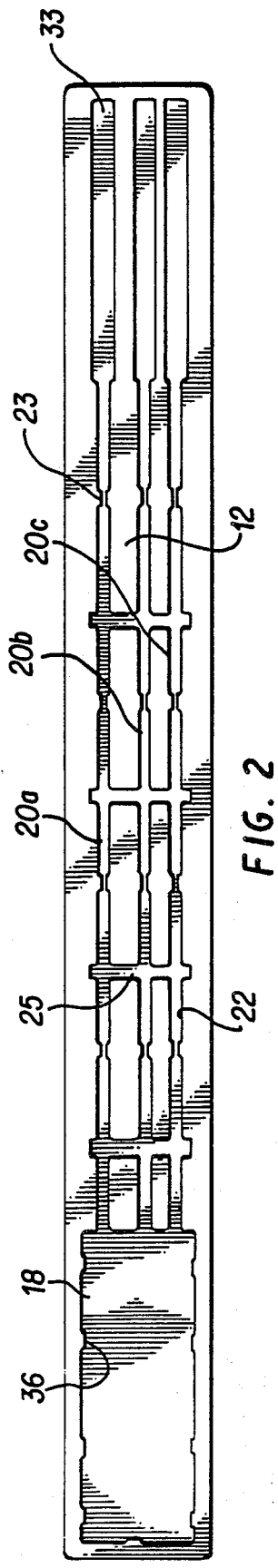
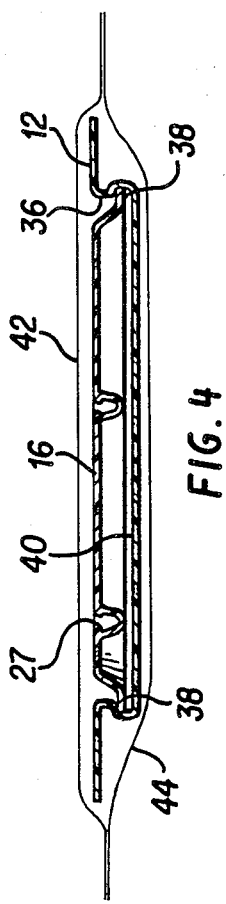
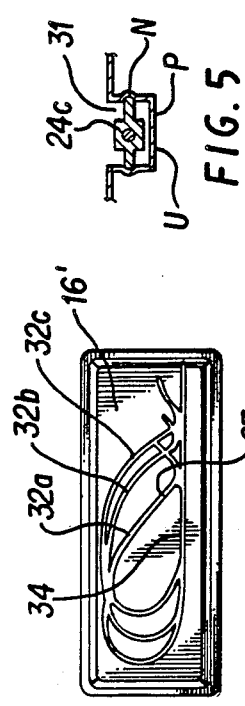

CATHETER PACKAGING SYSTEM

BACKGROUND OF THE INVENTION

1. Field of the Invention

The present invention relates to a catheter packaging system.

2. Description of the Prior Art

Because of the variety of catheters needed for specialized uses and the need for providing a packaging system which retains the catheters against distortion or damage during packaging, shipping, handling and storage, it has been found necessary in the prior art to employ a large number of different catheter trays in order to provide a catheter package specifically configured to maintain each catheter in its precise shape and condition prior to use. This requirement has resulted in large costs for tooling because specialized tooling must be provided for each tray. Further, the wide variety of trays required has resulted in the necessity to provide a substantial inventory at further cost.

By the present invention these problems of the prior art have been overcome and the cost of tooling and inventory has been significantly reduced while still insuring that each of the wide variety of catheters is securely retained in place in the package without risk of distortion or damage.

SUMMARY OF THE INVENTION

In accordance with the present invention, in one form thereof, a catheter packaging system is provided which comprises a catheter tray including a main tray body and an interchangeable insert receivable therein. The main tray body has a plurality of tracks for receiving and retaining the hub and body portions of catheters of different shapes, lengths and sizes. The interchangeable inserts are formed with a variety of different shapes of tracks for receiving catheter tips, each track of an insert being formed to conform to the the shape of the catheter tip to be accommodated therein. The main tray body is formed to include a recess for receiving any of the plurality of interchangeable inserts. Means are provided for retaining the insert securely in its assembled position. Each insert has a plurality of tip-retaining tracks therein and at least one of these tracks is disposed in line with one of the tracks in the main trap body.

BRIEF DESCRIPTION OF THE DRAWINGS

FIG. 1 is a top view of a catheter packaging system in accordance with the present invention, showing a main tray body and an interchangeable insert assembled therein.

FIG. 2 is a top view of the main tray body of the catheter packaging system shown in FIG. 1.

FIG. 3 is a top view of another interchangeable catheter tip-retaining insert of the catheter packaging system shown in FIG. 1.

FIG. 4 is an enlarged transverse cross-section through line 4—4 of FIG. 1.

FIG. 5 is an enlarged transverse cross-section through line 5—5 of FIG. 1.

DETAILED DESCRIPTION OF THE PREFERRED EMBODIMENT

Referring to the drawings, the catheter packaging system of this invention includes a catheter tray 10. Catheter tray 10 comprises two tray portions, namely an elongate main tray body 12 and an interchangeable catheter tip-retaining insert 16, the insert being assembled to the main tray body to form a complete tray. The main tray body includes a hub-retaining portion 14. The main tray body 12 and catheter tip-retaining insert 16 can be made by any suitable plastic material, such as polystyrene, glycol-modified polyethylene terephthalate (PETG), polyvinyl chloride (PVC), and the like.

The main tray body includes a keeper recess 18 at one end thereof, and each interchangeable insert 16 is formed to be selectively received and retained therein in a manner described in detail later in this specification. FIG. 1 illustrates the catheter tray with an insert assembled therein and a catheter in its packaged position. FIG. 2 illustrates the main tray body without the insert and without the catheter.

In the embodiments shown, the main tray body is elongate and has a plurality of linear catheter tracks 20a, 20b an 20c, molded longitudinally therein for holding catheters of different lengths, shapes and sizes. Each of the main body tracks 20a, 20b and 20c in FIG. 1 is provided with catheter-retaining edges 22 that extend inwardly at the upper surface of the tray in the configuration of an undercut ledge for snap-retaining the long body portion of a catheter, such as angiographic catheter 24, within a track. In the embodiment shown in FIG. 2, a plurality of inwardly extending tabs 23 are provided for snap-retaining the catheter within the track. The inwardly extending edges 22 or tabs 23 keep the catheter body within the corresponding main body track, yet allow the catheter to slide freely within the track. The main tray body is formed of a resiliently deformable plastic material that allows easy removal of a catheter and may be clear, opaque or translucent. In the embodiment shown in FIG. 2, stiffening cross slots 25 are molded into the main tray body to add rigidity thereto.

The interchangeable tip-retaining insert 16 shown in FIG. 1 includes a plurality of catheter tip tracks 26a, 26b, 26c and 26d for holding different catheter tips. Each of the tip tracks 26a, 26b, 26c and 26d is provided with catheter tip-retaining edges 27 that extend inwardly at the upper surface of the insert in the configuration of an undercut ledge, for holding a respective catheter tip. See FIGS. 1 and 4. Alternatively, catheter tips can be held within the catheter tip tracks of the insert by inwardly extending tabs that function in the same manner as tabs 23 shown in FIG. 2.

In the embodiment shown in FIG. 1, catheter tip tracks 26a and 26b converge to form a common catheter tip track 28 that is arranged in line with main body track 20a. Similarly, tip tracks 26c and 26d converge to form a common catheter tip track 30 that is in line with main body track 20b.

In the embodiment shown in FIG. 1, catheter 24 has a tip portion 24a which is held within tip track 26a, a body portion 24b which is held within main tray body track 20a, and a hub portion 24c held within hub-retaining slot 31. Hub portion 24c is snap-lockable within slot 31 by any suitable means. In the embodiment shown in detail in FIG. 5, hub portion 24c includes opposed hub projections P extending outwardly to engage corresponding locking notches N, which extend along the sidewalls of slot 31. Because the main tray body is formed of resiliently deformable material, the catheter hub is easily removed by pushing upwardly on the underside U of the tray from beneath the hub, to disengage the hub from the slot 31. Alternatively, the hub portion 24c can be slid backwardly in slot 31, and then up and out of slot 31 along inclined ramp 33 at the rear of slot 31. Ramp 33 farther provides an area for the hub portion to be flipped up and out of slot 31 by a finger. In the embodiments shown, the hub retaining slots 31 are elongate to accommodate catheters of different lengths.

FIG. 3 illustrates another tip-retaining insert 16' that is interchangeable with insert 16 of FIG. 1 in the keeper recess of the main tray body 12. Insert 16' includes a plurality of catheter tip tracks 32a, 32b and 32c molded therein that converge into a common catheter tip track 34. Common catheter tip track 34 is positioned to be in line with main body track 20c when insert 16' is inserted into keeper recess 18 of the main tray body 12.

As shown in FIGS. 1, 2 and 4, the main tray body 12 is formed with a plurality of keeper tabs 36 spaced along the periphery of the recess 18. The keeper tabs 36 project inwardly into the recess 18 of the main tray body 12. As best shown in FIG. 4 these keeper tabs 36 are spaced from the bottom 40 of the recess 18 to provide a space for receiving and retaining the insert 16. The insert 16, as best shown in FIG. 4, is formed with a peripheral outwardly extending lip portion 38 which, in the assembled position of the insert, is retained beneath the keeper tabs 36. Both the main tray body and the insert are formed of flexible plastic material so that the interchangeable insert may be snapped into its assembled position in the main tray body and retained therein by the engagement of the keeper tabs 36 with the lip portion 38.

In the embodiment shown, the catheter packaging assembly of tray 10 holding catheter 24 is sealed within a flexible pouch having a peelably removable transparent cover 42 that is formed of any suitable polymeric film material, such as polyethylene or polyester.

Transparent cover 42 is heat-sealed or bonded by appropriate means to a backing 44 formed of a suitable material such as paper or TYVEK ®, which is a spun-bonded polyolefin membrane used in sterile packaging. The backing 44 is gas permeable to permit sterilizing gases to enter the package.

Alternatively, gas-permeable paper or TYVEK ® can be sealed directly to the top of the main tray to enclose the catheter within the tray.

It can be seen that the interchangeable tip inserts of the present invention, each having a plurality of catheter tip tracks for different catheters, in combination with a main tray body also having a plurality of catheter tracks for different catheters, provides catheter packaging that is specifically configured for a large number of types of catheters, but with a minimum of tooling and inventory. This is accomplished by producing a limited number of "generic" main tray bodies having hub sections long enough to accommodate all required catheter lengths for a particular group of catheters, and employing a plurality of interchangeable inserts having tracks precisely configured for accommodating a wide variety of catheter tips to accommodate the plurality of catheter tips required for a variety of catheters provided for various specialized uses. The plurality of tip tracks present in each interchangeable tip insert further increases the number of types and sizes of catheters that can be specifically accommodated by the invention.

With catheter tip tracks formed precisely to the intended shape of each catheter tip, the tip track shapes will correct any minor shape deviations of the catheter tips that may arise during manufacturing, and prevent deviations during sterilization, shipment and storage. The catheter is held within the tracks while allowing the catheter to slide within the tracks to avoid deformation of the catheter during handling. Disposing the insert tip tracks in line with tray body tracks prevents kinking of the catheter tubing, and the tabs 36 retain each interchangeable insert within the recess.

Since many modifications, variations and changes in detail may be made to the described embodiment, it is intended that all matter in the foregoing description and shown in the accompanying drawings be interpreted as illustrative and not in a limiting sense.

We claim:

1. A catheter packaging system comprising a catheter tray, said catheter tray including a main tray body and an interchangeable insert selectively receivable in said main tray body, said main tray body having a recess therein and said insert being receivable in said recess, means for retaining said insert in assembled position within said recess, said main tray body having at least one first track therein, said first track being formed for retaining the body portion of a catheter therein, said insert including a plurality of second tracks, each of said second tracks being formed to receive a catheter tip therein, at least one of said second tracks being in line with said first track.

2. The catheter packaging system of claim 1 wherein said main tray body includes a plurality of first tracks therein, each of said first tracks being formed for retaining the body portion of a catheter therein, at least one of said first tracks being in line with at least one of said second tracks.

3. The catheter packaging system of claim 1, wherein the insert retaining means is comprised of keeper tabs extending inwardly into the recess from the main tray body.

4. The catheter packaging system of claim 1, wherein said first track includes tabs extending inwardly from the main tray body for retaining the body portion of a catheter therein.

5. The catheter packaging system of claim 1, wherein said first track includes a hub-retaining slot formed for holding the hub portion of a catheter therein.

6. The catheter packaging system of claim 5, wherein said hub-retaining slot includes locking notches for engaging a catheter hub to thereby retain the hub portion of a catheter therein.

7. The catheter packaging system of claim 5, wherein the hub-retaining slot is formed to accommodate catheters of different lengths.

8. The catheter packaging system of claim 1, wherein the main tray body of the catheter tray is elongate and said first track is linear and extends longitudinally along the main tray body.

9. A catheter packaging system comprising a catheter tray assembly, said catheter tray assembly including a main tray body and an interchangeable insert selectively receivable in said main tray body, said main tray body having a recess therein and said insert being receivable in said recess, means for retaining said insert in assembled position within said recess, said main tray body having at least one first track therein, said first track being formed for retaining the body portion of a catheter therein, said insert including a plurality of second tracks, each of said second tracks being formed to receive a catheter tip therein, at least one of said second tracks being in line with said first track, and a catheter held by the main tray body and the interchangeable insert within the in-line first and second tracks.

10. The catheter packaging system of claim 9, wherein the catheter tray assembly and the catheter held therein are sealed within a pouch having a gas permeable portion.

11. The catheter packaging system of claim 10 wherein said pouch has a removable cover sealed to the gas permeable portion.

12. The catheter packaging system of claim 9, wherein said first track includes a hub-retaining slot formed for retaining the hub portion of a catheter therein.

13. The catheter packaging system of claim 12 wherein the hub-retaining slot is formed to accommodate catheters of different lengths.

14. A catheter packaging system comprising a catheter tray, said catheter tray including a main tray body and an interchangeable insert selectively receivable in said main tray body, said main tray body having a recess therein and said insert being receivable in said recess, means for retaining said insert in assembled position within said recess, said main tray body having a plurality of first tracks therein, each of said first tracks being formed for retaining the body portion of a catheter therein, said insert including a plurality of second tracks, each of said second tracks being formed to receive a catheter tip therein, at least one of said second tracks being in line with one of said first tracks.

15. The catheter packaging system of claim 14, wherein each of said first tracks includes a hub-retaining slot formed for retaining the hub portion of a catheter therein.

16. The catheter packaging system of claim 15, whereing said hub-retaining slot is formed to accommodate catheters of different lengths.

* * * * *